US012678426B2

(12) United States Patent
Minamizono

(10) Patent No.: US 12,678,426 B2
(45) Date of Patent: Jul. 14, 2026

(54) PHARMACEUTICAL COMPOSITION

(71) Applicant: KOWA COMPANY, LTD., Nagoya (JP)

(72) Inventor: Akito Minamizono, Fuji (JP)

(73) Assignee: KOWA COMPANY, LTD., Nagoya (JP)

( * ) Notice: Subject to any disclaimer, the term of this patent is extended or adjusted under 35 U.S.C. 154(b) by 0 days.

(21) Appl. No.: 18/244,628

(22) Filed: Sep. 11, 2023

(65) Prior Publication Data

US 2023/0414578 A1 Dec. 28, 2023

Related U.S. Application Data

(63) Continuation of application No. 16/626,770, filed as application No. PCT/JP2018/024883 on Jun. 29, 2018, now abandoned.

(30) Foreign Application Priority Data

Jun. 30, 2017 (JP) ................................. 2017-128683

(51) Int. Cl.
*A61K 31/423* (2006.01)
*A61K 9/28* (2006.01)

(52) U.S. Cl.
CPC .......... *A61K 31/423* (2013.01); *A61K 9/2813* (2013.01); *A61K 9/282* (2013.01)

(58) Field of Classification Search
CPC ... A61K 9/2813; A61K 9/2806; A61K 9/2086
See application file for complete search history.

(56) References Cited

U.S. PATENT DOCUMENTS

| | | | |
|---|---|---|---|
| 5,439,687 A | 8/1995 | Compassi | |
| 9,572,798 B2 | 2/2017 | Takizawa | |
| 2005/0101636 A1 | 5/2005 | Yamazaki et al. | |
| 2011/0150945 A1 | 6/2011 | Spitz | |
| 2015/0132396 A1 | 5/2015 | Coulter et al. | |
| 2015/0196538 A1 | 7/2015 | Takizawa et al. | |
| 2016/0136138 A1 | 5/2016 | Shibata et al. | |
| 2016/0354315 A1 | 12/2016 | Li | |
| 2017/0079915 A1 | 3/2017 | Nomura et al. | |
| 2017/0143738 A1* | 5/2017 | Ando ........................ | A61P 3/06 |

FOREIGN PATENT DOCUMENTS

| | | |
|---|---|---|
| JP | 2015-218322 A | 12/2015 |
| JP | 2016-535055 A | 11/2016 |
| JP | 7007379 B2 | 2/2022 |
| WO | WO 2005/023777 A1 | 3/2005 |
| WO | WO 2007/083679 | 7/2007 |
| WO | WO 2014/050134 A1 | 4/2014 |
| WO | WO 2015/005365 A1 | 1/2015 |
| WO | WO 2015/141662 A1 | 9/2015 |
| WO | WO 2016/192680 A1 | 12/2016 |

OTHER PUBLICATIONS

Decision of Refusal issued on Aug. 22, 2023 in corresponding Japanese Patent Application No. 2022-000971 (with machine translation).

Yamazaki. Y. et al., "Enantioselective Synthesis of the PPARα Agonist (R)-K-13675 via (S)-2-Hydroxybutyrolactone". Synthesis, 2008, No. 7. pp. 1017-1022.

Hennuyer, N. et al., "The novel selective PPARα modulator (SPPARMα) pemafibrate improves dyslipidemia, enhances reverse cholesterol transport and decreases inflammation and atherosclerosis". Atherosclerosis. Mar. 4, 2016, vol. 249, pp. 200-208.

"Report on the deliberation results of parmodia tablets 0.1 mg," Pharmaceutical Evaluation Division of Pharmaceutical Safety and Environmental Health Bureau, Ministry of Health, Labour and Welfare, Jul. 3, 2017. (with partial English translation (pp. 5-6).

Fruchart, J. C., "Selective peroxisome proliferator-activated receptorα modulators (SPPARMα): The next generation of peroxisome proliferator-activated receptor α-agonists" Cardio Vascular Diabetology., 2013; vol. 12 No. 82, pp. 1-8.

International Search Report issued on Aug. 21, 2018 in PCT/JP2018/024883 filed on Jun. 29, 2018, 3 pages.

Office Action issued Jul. 26, 2022, in corresponding Japanese Patent Application No. 2018-126046 (with English Translation), 10 pages.

Ansel's Pharmaceutical Dosage Forms and Drug Delivery Systems, 2005, 8th ed. by Allen, et al, Lippincott Wiliams & Wilkins (Year: 2005), pp. 247-251.

* cited by examiner

*Primary Examiner* — Gina C Justice
(74) *Attorney, Agent, or Firm* — Oblon, McClelland, Maier & Neustadt, L.L.P.

(57) ABSTRACT

Provided is a pharmaceutical composition which contains pemafibrate, a salt thereof or a solvate thereof and one or more selected from the group consisting of a metal oxide, a dihydric alcohol, an ester species and a silicic acid compound and which has excellent storage stability. The pharmaceutical composition includes the following components (A) and (B):(A) pemafibrate, a salt thereof or a solvate thereof; and (B) one or more selected from the group consisting of the following components (B-1) to (B-4):(B-1) a metal oxide; (B-2) a dihydric alcohol; (B-3) an ester species; and (B-4) a silicic acid compound, with component (A) and component (B) being substantially in non-contact with each other.

20 Claims, No Drawings

PHARMACEUTICAL COMPOSITION

This application is a continuation of U.S. application Ser. No. 16/626,770, filed Dec. 26, 2019, pending, which is a 37.1 of application of PCT/JP2018/024883, filed Jun. 29, 2018 and claims benefit of Japanese Application No. 2017-128683, filed Jun. 30, 2017. The contents of each of these applications are incorporated herein by reference in their entirety.

FIELD OF THE INVENTION

The present invention relates to a pharmaceutical composition etc.

BACKGROUND OF THE INVENT ION

It in known that pemafibrate (Chemical Names: (2)-2 [3-([1,3-Benzoxazol-2-yl[3-(4-methoxyphenoxy)propyl] amino]methyl)phenoxy]butanoic acid) (International Non-proprietary Name: pemafibrate) represented by the following structural formula:

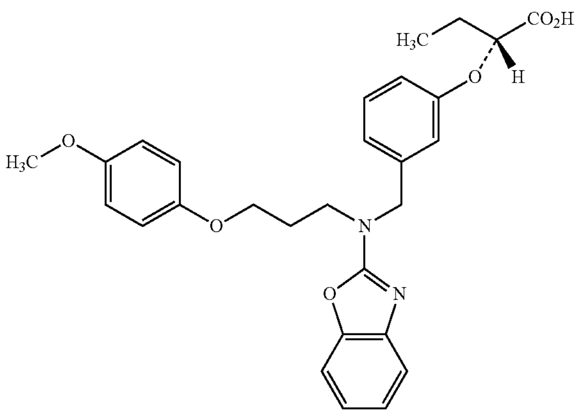

a salt thereof or a solvate thereof has excellent PPAR-α agonist activity, exhibits plasma triglyceride concentration reducing action, HDL cholesterol increasing action, etc., and is useful for prevention and treatment of dyslipidemia (hyperlipidemia) (Patent Document 1 and Non-Patent Documents 1 and 2), and useful for prevention and treatment of NAFLD (non-alcoholic fatty liver disease) (Patent Document 2).

Meanwhile, a compound useful as an active component for a pharmaceutical preparation is normally formulated as some pharmaceutical composition, and administered, and it is not unusual that a long time passes until a pharmaceutical composition is administered after production of the pharmaceutical composition. Thus, from the viewpoint of exhibiting expected drug efficacy and avoiding unanticipated adverse side effects, it is very important to secure storage stability of active components in the pharmaceutical composition.

PRIOR ART DOCUMENTS

Patent Documents

Patent Document 1: International Publication No. WO 2005/023777

Patent Document 2: International Publication No. WO 2015/005365

Non-Patent Documents

Non-Patent Document 1: Yukiyoshi Yamazaki, et al., Synthesis, 2008(7), 1017-1022.

Non-Patent Document 2: Fruchart J C., Cardiovasc Diabetol., 2013; 12: 82.

SUMMARY OF THE INVENTION

Problems to be Solved by the Invention

However, storage stability of active components significantly depends on the physical and chemical properties of components, but it is often impossible to predict such properties from the chemical structures or the like of the components, and there are not a few cases where a problem becomes evident only when a pharmaceutical composition is actually produced. Thus, establishment of a technique for securing storage stability of active components in a pharmaceutical composition commonly requires considerable try and error.

Pemafibrate, a salt thereof or a solvate thereof has been only reported to exhibit the above-described pharmacological effects, and has heretofore not been specifically studied in terms of a pharmaceutical composition, and storage stability in a pharmaceutical composition has heretofore not been reported at all.

Thus, for developing a pharmaceutical composition containing pemafibrate, a salt thereof or a solvate thereof, the present inventor has studied formulation using various additives for pharmaceutical preparation. Surprisingly, the inventor has found that when a pharmaceutical composition is stored which is produced by mixing pemafibrate, a salt thereof or a solvate thereof (hereinafter, sometimes referred to simply as "component (A)") with any of the following components 1 to 4 (hereinafter, components 1 to 4 are sometimes referred to as "component (B-1)", "component (B-2)", "component (B-3)" and "component (B-4)", respectively, and "one or more selected from the group consisting of component (B-1), component (B-2), component (B-3) and component (B-4)" is sometimes referred to as "component (B)"):

1. metal oxide typified by titanium oxide;
2. dihydric alcohol typified by macrogol;
3. ester species typified by triethyl citrate; and
4. silicic acid compound typified by light anhydrous silicic acid, an interaction between component (A) and component (B) is observed, and the amount of decomposition products (related substances) of pemafibrate increases, leading to development of problems with storage stability.

Thus, an object of the present invention is to provide a pharmaceutical composition which contains pemafibrate, a salt thereof or a solvate thereof and one or more selected from the group consisting of a metal oxide, a dihydric alcohol, an ester species and a silicic acid compound and which has excellent storage stability.

Means for Solving the Problems

In order to solve the problem with the storage stability affected by an interaction between pemafibrate, a salt thereof or a solvate thereof and any of the components 1 to 4, the present inventor has further extensively conducted studies, and resultantly found that physical contact between pemafibrate, a salt thereof or a solvate thereof and any of the components 1 to 4 is a cause of the interaction, and by incorporating pemafibrate, a salt thereof or a solvate thereof and any of the components 1 to 4 in a pharmaceutical composition in such a manner that both the components are hardly in direct contact with each other, increase in the amount of decomposition products of pemafibrate is suppressed, so that excellent storage stability is obtained. The present invention has been accomplished on the basis of this finding.

Accordingly, the present invention provides a pharmaceutical composition comprising the following components (A) and (B):

(A) pemafibrate, a salt thereof or a solvate thereof; and (B) one or more selected from the group consisting of the following components (B-1) to (B-4):

(B-1) a metal oxide;

(B-2) a dihydric alcohol;

(B-3) an ester species; and (B-4) a silicic acid compound, wherein component (A) and component (B) are substantially in non-contact with each other.

The present invention also provides a method for stabilizing pemafibrate, a salt thereof or a solvate thereof in a pharmaceutical composition, the method comprising the step of incorporating the following components (A) and (B):

(A) pemafibrate, a salt thereof or a solvate thereof; and (B) one or more selected from the group consisting of the following components (B-1) to (B-4):

(B-1) a metal oxide;

(B-2) a dihydric alcohol;

(B-3) an ester species; and (B-4) a silicic acid compound, wherein component (A) and component (B) are substantially in non-contact with each other.

Effects of the Invention

According to the present invention, it is possible to provide a pharmaceutical composition in which increase in the amount of decomposition products of pemafibrate is suppressed to exhibit excellent storage stability.

DETAILED DESCRIPTION OF THE INVENTION

<Pemafibrate, Salt Thereof or Solvate Thereof (Component (A))>

Herein, "pemafibrate, a salt thereof or a solvate thereof" includes pemafibrate (Chemical Name: (2R)-2-[3-([1,3-Benzoxazol-2-yl[3-(4-methoxyphenoxy)propyl]amino]methyl)phenoxy]butanoic acid) (International Nonproprietary Name: pemafibrate) itself, a pharmaceutically acceptable salt of pemafibrate and a solvate of pemafibrate or a pharmaceutically acceptable salt thereof with water, alcohol (for example ethanol) or the like. The pharmaceutically acceptable salt is not particularly limited, and examples thereof include acid addition salts and base addition salts. Specific examples of the acid addition salts include acid addition salts with inorganic acids, such as hydrochlorides, hydrobromides, hydroiodides, sulfate salts, nitrate salts and phosphate salts; and acid addition salts with organic acids, such as benzoate salts, methanesulfonate salts, ethanesulfonate salts, benzenesulfonate salts, p-toluenesulfonate salts, maleate salts, fumarate salts, tartrate salts, citrate salts and acetate salts. Specific examples of the base addition salts include metal salts such as sodium salts, potassium salts, lithium salts, calcium salts and magnesium salts; salts with amines such as ammonia, trimethylamine, triethylamine, pyridine, collidine and lutidine; and base addition salts with organic bases such as lysine, arginine, cinchonine and cinchonidine.

Pemafibrate, a salt thereof or a solvate thereof is a known compound, and can be produced through a method as disclosed in Patent Document 1, Non-Patent Document 1 or U.S. Pat. No. 7,109,226, for example. In the present invention, a pemafibrate crystal which can be produced through the method described in Non-Patent Document 1 (preferably a crystal showing a melting point of 95 to 101° C., particularly preferably 97 to 100° C. in measurement performed in accordance with The Japanese Pharmacopoeia, 17th Edition, Melting Point Determination Method 1) is preferably used. The disclosures of the documents are incorporated herein by reference.

The content of pemafibrate, a salt thereof or a solvate thereof in the pharmaceutical composition is not particularly limited, and can be determined in appropriate consideration of the type of preparation, the sex, age and symptoms of a patient in need of the composition, and the like. For example, the content can be set so that the daily dose of pemafibrate, a salt thereof or a solvate thereof may be 0.05 to 0.8 mg, more preferably 0.075 to 0.6 mg, particularly preferably 0.1 to 0.4 mg, in terms of a free form of pemafibrate.

The content of pemafibrate, a salt thereof or a solvate thereof in the pharmaceutical composition is preferably 0.001 to 60 mass %, more preferably 0.005 to 25 mass %, still more preferably 0.01 to 10 mass %, yet more preferably 0.05 to 5 mass %, particularly preferably 0.05 to 0.5 mass %, in terms of a free form of pemafibrate, with respect to the total mass of the pharmaceutical composition.

<Metal Oxide (Component (B-1))>

Herein, the "metal oxide" means an oxide of a metal such as a typical metal or a transition metal, and the type of the metal is not particularly limited. Examples of the metal include metals of Group 2 elements (magnesium, calcium, etc.), transition metals (titanium, iron, etc.), metals of Group 12 elements (zinc etc.) and metals of Group 13 elements (aluminum etc.). Among them, an oxide of a metal selected from the group consisting of a metal of Group 2 elements and a transition metal is preferable, and an oxide of a metal selected from the group consisting of magnesium, titanium and iron is more preferable.

Specific examples of the metal oxide include yellow oxide of iron, red ferric oxide, yellow ferric oxide, brown iron oxide, black iron oxide, synthetic hydrotalcite, zinc oxide, aluminum oxide, calcium oxide, titanium oxide and magnesium oxide, and these metal oxides may be used singly, or in combinations of two or more thereof. Among them, yellow oxide of iron, red ferric oxide, yellow ferric oxide, brown iron oxide, black iron oxide, synthetic hydrotalcite, titanium oxide and magnesium oxide are preferable, and yellow oxide of iron, red ferric oxide, yellow ferric oxide, brown iron oxide, black iron oxide, titanium oxide and magnesium oxide are more preferable, with titanium oxide being particularly preferable.

Each of these metal oxides is a known component. The metal oxides may be produced through a known method, or commercially available products may be used. Examples of the commercially available products include Apasit (Fuji Chemical Industries Co., Ltd.), ALCAMAC (Kyowa Chemical industry Co., Ltd.), Synthetic Hydrotalcite (Tomita Pharmaceutical Co., Ltd.), Magnesium Oxide (Tomita Pharmaceutical Co., Ltd.), Yellow Ferric Oxide (San-Si Gen F.F.I., Inc.), Black Iron Oxide (San-Ei Gen F.F.I., Inc.), Titanium Oxide (Toho Titanium Co., Ltd.) and Red Ferric Oxide (San-Ei Gen F.F.I., Inc.).

The content of metal oxides in the pharmaceutical composition is not particularly limited, and can be determined in appropriate consideration of the type of preparation, the sex, age and symptoms of a patient in need of the composition, and the like, but the total amount of the metal oxides with respect to the total mass of the pharmaceutical composition is preferably 0.001 to 60 mass %, more preferably 0.005 to 0.3 mass %, still more preferably 0.01 to 2 mass %, particularly preferably 0.1 to 1 mass %.

The mass ratio between the content of pemafibrate, a salt thereof or a solvate thereof and the content of the metal oxides in the pharmaceutical composition is not particularly limited, and the total content of the metal oxides with respect to 1 part by mass of a free form of pemafibrate is preferably 0.01 to 30 parts by mass, more preferably 0.05 to 20 parts by mass, particularly preferably 0.1 to 10 parts by mass.

<Dihydric Alcohol (Component (B-2))>

Herein, the "dihydric alcohol" means a compound having two alcoholic hydroxyl groups, and may be either a non-polymer or a polymer. Specific examples of the dihydric alcohol include alkylene glycols such as ethylene glycol, propylene glycol, 1,3-propanediol, 2-methyl-1,3-propanediol and 1,3-butanediol; and polyalkylene glycols such as diethylene glycol, dipropylene glycol, macrogol (for example macrogol 100, macrogol 200, macrogol 300, macrogol 400, macrogol 600, macrogol 1000, macrogol 1500, macrogol 1540, macrogol 4000, macrogol 6000, polyethylene glycol 8000, macrogol 20000 and macrogol 35000), polypropylene glycol (for example polypropylene glycol 2000), polyoxyethylene polyoxypropylene glycol (for example polyoxyethylene (3) polyoxypropylene (17) glycol, polyoxyethylene (20) polyoxypropylene (20) glycol, polyoxyethylene (42) polyoxypropylene (67) glycol, polyoxyethylene (54) polyoxypropylene glycol, polyoxyethylene (105) polyoxypropylene (5) glycol, polyoxyethylene (120) polyoxypropylene glycol, polyoxyethylene (124) polyoxypropylene (39) glycol, polyoxyethylene (160) polyoxypropylene (30) glycol, polyoxyethylene (196) polyoxypropylene (67) glycol and polyoxyethylene (200) polyoxypropylene (70) glycol. These dihydric alcohols may be used singly, or in combinations of two or more thereof.

The dihydric alcohol is preferably a polyalkylene glycol, more preferably macrogol, still more preferably one or more selected from the group consisting of macrogol 100, macrogol 200, macrogol 300, macrogol 400, macrogol 600, macrogol 1000, macrogol 1500, macrogol 1540, macrogol 4000, macrogol 6000, polyethylene glycol 8000, macrogol 20000 and macrogol 35000, particularly preferably macrogol 6000. The dihydric alcohol is preferably macrogol having an average molecular weight of 100 to 20,000, more preferably macrogol having an average molecular weight of 200 to 10,000, particularly preferably macrogol having an average molecular weight of 300 to 8,000. The average molecular weight of macrogol can be measured in accordance with "Average Molecular Mass" described in The Japanese Pharmacopoeia, 17th Edition, Pharmaceutical Preparations, "Macrogol 400".

Each of these dihydric alcohols is a known component. The dihydric alcohols may be produced through a known method, or commercially available products may be used. Examples of the commercially available products include Kollisolv PG (BASF Japan Ltd.), Diethylene Glycol (Nippon Shokubai Co., Ltd.), UNISAFE DPG-R (NOF CORPORATION), Macrogol 200 (Sanyo Chemical Industries, Ltd.), Kollisolv PEG300 (BASF Japan Ltd.), SUPER REFINED PEG 400 (Croda Japan K.K.), CARBOWAX Sentry PEG 600 (Dow Chemical Japan Limited), Macrogol 1000 (NOF CORPORATION), Macrogol 1500 (Sanyo Chemical Industries, Ltd.), CARBOWAX Sentry PEG 1540 (Dow Chemical Japan Limited), Macrogol 4000 (Sanyo Chemical Industries, Ltd.), Macrogol 6000 (Sanyo Chemical Industries, Ltd.), Macrogol 20000 (Sanyo Chemical Industries, Ltd.), NEWPOL PP-2000 (Sanyo Chemical Industries, Ltd.), PRONON 101P (NOF CORPORATION), Kollisolv P124 (BASF Japan Ltd.), PRONON 403P (NOF CORPORATION), NEWDET PE-85 (Sanyo Chemical Industries, Ltd.), PEP-101 (Freund Corporation), Kolliphor P188 (BASF Japan Ltd.), Kolliphor P407 Micro (BASF Japan Ltd.) and UNILUBE DP-950B (NOF CORPORATION).

The content of dihydric alcohols in the pharmaceutical composition is not particularly limited, and can be determined in appropriate consideration of the type of preparation, the sex, age and symptoms of a patient in need of the composition, and the like, but the total amount of the dihydric alcohols with respect to the total mass of the pharmaceutical composition is preferably 0.005 to 95 mass %, more preferably 0.11 to 60 mass %, still more preferably 0.01 to 5 mass %, yet more preferably 0.05 to 3 mass %, particularly preferably 0.1 to 1 mass %.

The mass ratio between the content of pemafibrate, a salt thereof or a solvate thereof and the content of the dihydric alcohols in the pharmaceutical composition is not particularly limited, and the total content of the dihydric alcohols with respect to 1 part by mass of a free form of pemafibrate is preferably 0.1 to 30 parts by mass, more preferably 0.5 to 20 parts by mass, particularly preferably 1 to 10 parts by mass.

<Ester Species (Component (B-3))>

Herein, the "ester species" means a compound having one or more (preferably 1 to 4, more preferably 2 to 4, particularly preferably 3 to 4) ester bonds in the molecule thereof. The carboxylic acid/alcohol forming the ester bond is not particularly limited, and examples of the ester species include esters of a monovalent carboxylic acid such as acetic acid, butyric acid, lauric acid, palmitic acid, stearic acid, oleic acid or sesquioleic acid or a polyvalent carboxylic acid such as citric acid or phthalic acid and a monohydric alcohol such as ethanol, butanol or tocopherol or a polyvalent alcohol such as glycerin, polyglycerin, propylene glycol, sorbitol, sorbitan or sucrose.

Specific examples of the ester species include sorbitan fatty acid ester, sorbitan sesquioleate, glycerin fatty acid ester, medium-chain triglyceride, diethyl phthalate, dibutyl phthalate, butyl-phthalyl-butyl glycolate, sucrose fatty acid ester, propylene glycol fatty acid ester, dioctyl sodium sulfosuccinate, acetyltriethyl citrate, acetyltributyl citrate, triethyl citrate, tributyl citrate, triacetin, tocopherol acetate, polyoxyethylene hydrogenated castor oil (polyoxyethylene hydrogenated castor oil 40, polyoxyethylene hydrogenated castor oil 60, etc.), polyoxyethylene sorbitan fatty acid ester (polysorbate 20, polysorbate 40, polysorbate 60, polysorbate 80, etc.), aminoalkyl methacrylate copolymer E, aminoalkyl methacrylate copolymer RS, polyvinylacetal diethylaminoacetate, hydroxypropylmethylcellulose acetate succinate, hydroxypropylmethylcellulose phthalate and sodium stearyl fumarate. These ester species may be used singly, or in combinations of two or more thereof.

The ester species is preferably a compound having 2 to 4 ester bonds in the molecule thereof, more preferably a diester or triester of a polyvalent carboxylic acid selected from the group consisting of citric acid and phthalic acid and an alcohol (preferably monohydric alcohol), a tetraester having citrate residues (alkanoyl-trialkyl citrate), or a triester of glycerin and a carboxylic acid (preferably monovalent carboxylic acid), still more preferably a triester of citric acid and an alcohol, a tetraester having citrate residues, or a triester of glycerin and a carboxylic acid, yet more preferably acetyltriethyl citrate, acetyltributyl citrate, triethyl citrate, tributyl citrate or triacetin, particularly preferably triethyl citrate or triacetin.

Each of these ester species is a known component. The ester species may be produced through a known method, or commercially available products may be used. Examples of the commercially available products include Food Additive NONION PP-40R (NOF CORPORATION), Food Additive NONION SP-60R (NOF CORPORATION), Food Additive NONION SP-60RP (NOF CORPORATION), Food Additive NONION OP-80R (NOF CORPORATION), Food Additive NONION CP-08R (NOF CORPORATION) NIKKOL AO-5MV (Nikko Chemicals Co., Ltd.), POEM 3-100 (RIKEN VITAMIN CO., LTD.), POEM HB (RIKEN VITAMIN CO., LTD.), POEM J-0381V (RIKEN VITAMIN CO., LTD.), POEM J-2081 (RIKEN VITAMIN CO., LTD.), POEM TR-FB (RIKEN VITAMIN CO., LTD.), POEM W-10 (RIKEN VITAMIN CO., LTD.), POEM W-60 (RIKEN VITAMIN CO., LTD.), Japanese Pharmaceutical Excipients PANACET 800 (NOF CORPORATION), Japanese Pharmaceutical Excipients PANACET 810 (NOF CORPORATION), Japanese Pharmaceutical Excipients PANACET 8105 (NOF CORPORATION), DX Ester F-160 (DKS Co., Ltd.), DK Ester F-140 (DKS Co., Ltd.), DK Ester F-110 (DKS Co., Ltd.), DX Ester F-90 (DKS Co., Ltd.), DX Eater F-70 (DKS Co., Ltd.), DX Ester F-50 (DKS Co., Ltd.), DK Ester F-20W (DKS Co., Ltd.). DX Ester F-10 (DES Co., Ltd.), DK Ester FA-10E (DES Co., Ltd.), NIKKOL Sefsol-218 (Nikko Chemicals Co., Ltd.), NIKKOL Sefsol-228 (Nikko Chemicals Co., Ltd.), CITROFLEX 2 (SC-60) (San-Ei Gen F.F.I., Inc.), Triacetin (YUKI GOSEI KOGYO CO., LTD.), RAPISOL (NOF CORPORATION), NIKKOL HCO-40 (Nikko Chemicals Co., Ltd.), NIKKOL HCO-60 (Nikko Chemicals Co., Ltd.), NIKKOL TL-10 (Nikko Chemicals Co., Ltd.), NIKKOL TP-10EX (Nikko Chemicals Co., Ltd.), NIKKOL TS-10MV (Nikko Chemicals Co., Ltd.), NIKKOL TO-10MV (Nikko Chemicals Co., Ltd.), EUDRAGIT E100 (HIGUCHI LTD.), EUDRAGIT RL100 (HIGUCHI LTD.), AEA “Sankyo” (SANKYO LIFETECH CO., LTD.), HPMCP (Shin-Etsu Chemical Co., Ltd.), Shin-Etsu AQOAT (Shin-Etsu Chemical Co., Ltd.) and PRUV (Kimura Sangyo Co., Ltd.).

The content of an ester species in the pharmaceutical composition is not particularly limited, and can be determined in appropriate consideration of the type of preparation, the sex, age and symptoms of a patient in need of the composition, and the like, and the total amount of the ester species with respect to the total mass of the pharmaceutical composition is preferably 0.005 to 60 mass %, more preferably 0.01 to 5 mass %, still more preferably 0.05 to 3 mass %, particularly preferably 0.1 to 1 mass %.

The mass ratio between the content of pemafibrate, a salt thereof or a solvate thereof and the content of the ester species in the pharmaceutical composition is not particularly limited, and the total content of the ester species with respect to 1 part by mass of a free form of pemafibrate is preferably 0.01 to 30 parts by mass, more preferably 0.05 to 20 parts by mass, particularly preferably 0.1 to 10 parts by mass.

<Silicic Acid Compound (Component (B-4))>

Herein, the “silicic acid compounds” include silicic acid compounds themselves, and salts of silicic acid compounds. Examples of the salts of silicic acid compounds include inorganic salts, and specific examples thereof include alkali metal salts such as sodium salts and potassium salts; salts with metals of Group 2 elements, such as magnesium salts and calcium salts; and salts with metals of Group 13 elements, such as aluminum salts.

Specific examples of the silicic acid compounds include hydrous silicic acid compounds or salts thereof such as hydrated silicon dioxide, amorphous silicon oxide hydrate, hydrous magnesium silicate and hydrous magnesium silicate (natural); anhydrous silicic acids or salts thereof such as light anhydrous silicic acid and heavy anhydrous silicic acid; silicic acids or salts thereof such as silicon dioxide, natural aluminum silicate, synthetic aluminum silicate, synthetic sodium magnesium silicate, calcium silicate, magnesium silicate, aluminum magnesium silicate, magnesium aluminosilicate and magnesium aluminometasilicate; diatomaceous earth; bentonite; kaolin; and talc, and these compounds may be used singly, or in combinations of two or more thereof.

The silicic compound is preferably anhydrous silicic acid or a salt thereof, particularly preferably light anhydrous silicic acid.

Each of these silicic acid compounds is a known component. The silicic acid compounds may be produced through a known method, or commercially available products may be used. Examples of the commercially available products include Neusilin A (Fuji Chemical Industries Co., Ltd.), FLORITE (Tomita Pharmaceutical Co., Ltd.), Magnesium Silicate (Tomita Pharmaceutical Co., Ltd.), VEEGUMI GRANULE (Sanyo Chemical Industries, Ltd.), VEEGUMI HV GRANULE (Sanyo Chemical Industries, Ltd.), VEEGUMI K GRANULE (Sanyo Chemical Industries, Ltd.), VEEGUMI F (Sanyo Chemical Industries, Ltd.), SYLYSIA 320 (FUJI SILYSIA CHEMICAL LTD.), SYLYSIA 350 (FUJI SILYSIA CHEMICAL LTD.), SYLYSIA 320TP (FUJI SILYSIA CHEMICAL LTD.), SYLYSIA 320FCP (FUJI SILYSIA CHEMICAL LTD.), MICON FR (Tomita Pharmaceutical Co., Ltd.), Silicon Dioxide (NIPPON AEROSIL CO., LTD.), Adsolider 101 (Freund Corporation), Adsolider 102 (Freund Corporation), SYLYSIA (FUJI SILYSIA CHEMICAL LTD.), SYLOSPHERE (FUJI SILYSIA CHEMICAL LTD.), Hydrous Amorphous Silicon Oxide (Tosoh Silica Corporation), Neusilin (Fuji Chemical Industries Co., Ltd.), Diatomaceous Earth (Shows Kako Corporation) and Talc (San-Ei Gen F.F.I., Inc.).

The content of silicic acid compounds in the pharmaceutical composition is not particularly limited, and can be determined in appropriate consideration of the type of preparation, the sex, age and symptoms of a patient in need of the composition, and the like, and the total amount of the silicic acid compounds with respect to the total mass of the pharmaceutical composition is preferably 0.001 to 95 maser, more preferably 0.005 to 60 mass %, still more preferably 0.01 to 5 maser, yet more preferably 0.05 to 3 mass %, particularly preferably 0.1 to 1 mass %.

The mass ratio between the content of pemafibrate, a salt thereof or a solvate thereof and the content of the silicic acid compounds in the pharmaceutical composition is not particularly limited, and the total content of the silicic acid compounds with respect to 1 part by mass of a free form of pemafibrate is preferably 0.01 to 30 parts by mass, more preferably 0.05 to 20 parts by mass, particularly preferably 0.1 to 10 parts by mass.

The total content of component (B) in the pharmaceutical composition is not particularly limited, and can be determined in appropriate consideration of the type of preparation, the sex, age and symptoms of a patient in need of the composition, and the like, but is preferably 0.01 to 95 mass %, more preferably 0.05 to 60 mass %, still more preferably 0.1 to 10 mass % particularly preferably 0.5 to 5 mass %, with respect to the total mass of the pharmaceutical composition.

The mass ratio between the content of pemafibrate, a salt thereof or a solvate thereof and the total content of component (B) in the pharmaceutical composition is not particularly limited, and the total content of component (B) with respect to 1 part by mass of a free form of pemafibrate is preferably 0.005 to 15 parts by mass, more preferably 0.01 to 1.0 parts by mass, still more preferably 0.05 to 5 parts by mass, particularly preferably 0.1 to 2 parts by mass.

As used herein, the expression "component (A) and component (B) are substantially in non-contact with each other" means that component (A) and component (B) are contained in the same pharmaceutical composition while contact between the components is avoided or suppressed to the extent that an interaction between the components causes substantially no problem. Therefore, as long as the interaction causes substantially no problem, pemafibrate and component (B) may be in contact with or in the vicinity of each other. Here, specific examples of the aspect in which "component (A) and component (B) are substantially in non-contact with each other" include aspects in which in addition to component (A) and component (B) in the pharmaceutical composition, other components (additives for pharmaceutical preparation, etc.) are co-present, and the presence of such other components prevents contact between component (A) and component (B) to the extent that an interaction between the components causes substantially no problem (e.g. such other components are disposed on the surfaces of component (A) and/or component (B) to prevent contact between component (A) and component (B) to the extent that an interaction between the components causes substantially no problem).

The pharmaceutical composition of the present invention may be one containing component (B) such that any one selected from the group consisting of component (B-1), component (B-2), component (B-3) and component (B-4) is substantially in non-contact with component (A), and from the viewpoint of suppressing increase in the amount of decomposition products of pemafibrate, aspects are particularly preferable in which all of component (B) blended in the pharmaceutical composition are substantially in non-contact with component (A). In view of the fact that as shown in Test Examples below, in particular, the amount of decomposition products of pemafibrate markedly increases in mixing with component (B-1), component (B-2) and component (B-3), aspects are preferable in which component (A) is substantially in non-contact with one or more selected from the group consisting of component (B-1), component (B-2) and component (B-3) from the viewpoint of suppressing increase in the amount of decomposition products of pemafibrate. In particular, among these aspects, aspects are preferable in which all of one or more selected from the group consisting of component (B-1), component (B-2) and component (B-3) contained in the pharmaceutical composition, are substantially in non-contact with component (A).

Herein, the dosage form of the "pharmaceutical composition" is not particularly limited, may be a solid, semisolid or liquid preparation, and can be selected according to the use purpose of the pharmaceutical composition. Examples of the dosage form of the pharmaceutical composition include dosage forms described in The Japanese Pharmacopoeia, 17th Edition, General Rules for Preparations. Specific examples of the peroral dosage form include solid preparations such as tablets (e.g. normal tablets, orally disintegrating tablets, chewable tablets, effervescent tablets, dispersion tablets and soluble tablets), capsules, granules (e.g. effervescent granules), powders and pills; semisolid preparations such as peroral jellies; liquid preparations such as peroral liquids (e.g. elixirs, suspensions, emulsions and lemonades). Examples of the parenteral dosage form include injections, inhalations, eye drops, ear drops, nasal drops, suppositories, solid external preparations, liquid external preparations, sprays, ointments, creams, gels and patches.

From the viewpoint of ease of administration and ease of production, the dosage form of the pharmaceutical composition is preferably a solid preparation, particularly preferably a solid preparation selected from the group consisting of a tablet. (e.g. normal tablet, orally disintegrating tablet, chewable tablet, effervescent tablet, dispersion tablet or soluble tablet), a capsule, a granule (e.g. effervescent granule), a powder and a pill. When the pharmaceutical composition is a solid preparation, movement (flowing) of component (A) and component (B) in the pharmaceutical composition is restricted, and therefore it is easier to ensure that both the components are "substantially in non-contact with each other".

Specific examples of the solid preparation include solid preparations containing: (I) component (A) itself or a solid composition containing component (A) (hereinafter, the solid composition is referred to as "solid composition (I)"); and (II) component (B) itself or a solid composition containing component (B) (hereinafter, the solid composition is referred to as "solid composition (II)"), with component (A) and component (B) being substantially in non-contact with each other (except for the case where (I) is component (A) itself and (IT) is component (B) itself). That is, it is preferable that one or both of component (A) and component (B) are in the form of a solid composition, with component (A) and component (B) being substantially in non-contact with each other.

In such aspects, components forming solid composition (I) and/or (II) (components other than component (A) and component (B) (additives for pharmaceutical preparation, etc.)) prevent contact between component (A) and component (B).

In such aspects, the form of the solid composition is not particularly limited, and examples thereof include forms such as powder forms (e.g. ground component (A) or component (B) coated with other components); grain form (e.g. component (A) or component (B) granulated together with other components); and tablet forms (e.g. component (A) or component (B) pelletized together with other components). The size of the solid composition is not particularly limited.

Here, the content of solid composition (I) is not particularly limited, and is preferably 15 to 99 mans %, more preferably 90 to 99 mass %, particularly preferably 94 to 98 mass %, with respect to the total mass of the solid preparation.

In solid composition (I), the total content of component (A) is not particularly limited, and is preferably 0.001 to 10 mass %, more preferably 0.01 to 7 mass %, particularly preferably 0.05 to 5 mass %, with respect to the total mass of solid composition (I).

The content of solid composition (II) is not particularly limited, and is preferably 1 to 85 mass %, more preferably 1 to 10 mass %, particularly preferably 2 to 6 mass %, with respect to the total mass of the solid preparation.

In solid composition (II), the total content of component (B) is not particularly limited, and is preferably 0.1 to 70 mass %, more preferably 1 to 60 mass %, particularly preferably 5 to 50 mass % with respect to the total mass of solid composition (II).

When solid composition (II) contains component (B-1), the total content of component (B-1) is not particularly limited, and is preferably 0.05 to 60 mass %, more preferably 0.5 to 50 mass's, particularly preferably 5 to 40 mass %, with respect to the total mass of solid composition (II).

When solid composition (II) contains component (B-2), the total content of component (B-2) is not particularly limited, and is preferably 0.1 to 30 mass %, more preferably 0.5 to 20 mass %, particularly preferably 1 to 15 mass %, with respect to the total mass of solid composition (II).

When solid composition (II) contains component (B-3), the total content of component (B-3) is not particularly limited, and is preferably 0.1 to 40 mass %, more preferably 1 to 30 mass %, particularly preferably 2 to 20 mass %, with respect to the total mass of solid composition (II).

When solid composition (II) contains component (B-4), the total content of component (B-4) is not particularly limited, and is preferably 0.1 to 50 mass %, more preferably 1 to 40 mass %, particularly preferably 3 to 35 mass %, with respect to the total mass of solid composition (II).

Examples of specific forms of the solid preparation in the aspects described above include the following <1> to <8>. These solid preparations may be produced and formulated through a known method, e.g., a method described in The Japanese Pharmacopoeia, 17th Edition, "General Rules for Preparations", by use of any additives for pharmaceutical preparation.

<1> A solid preparation produced by granulating any one of component (A) and component (B) together with appropriate components through an appropriate technique, adding the powdered product or granulated product to the non-granulated counterpart to thereby provide a powder or a granule, and optionally coating the powder or the granule with an appropriate material through an appropriate technique.

<2> A solid preparation produced by granulating component (A) and component (B) individually together with appropriate components through an appropriate technique, and optionally coating a powder or a granule containing the powdered product or granulated product with an appropriate material through an appropriate technique.

<3> A capsule including the solid preparation produced through the method in <1> or <2>, which is a powder or a granule optionally coated with an appropriate material through an appropriate technique.

<4> A solid preparation produced by pelletizing, through an appropriate technique, the powdered product or granulated product produced through the method in <1>, and the non-granulated counterpart, to thereby provide a tablet, and optionally coating the tablet with an appropriate material through an appropriate technique (sugar-coated tablet, film-coated tablet, etc.); or a solid preparation produced by pelletizing, through an appropriate technique, the powdered product or granulated product produced through the method in <2>, to thereby provide a tablet, and optionally coating the tablet with an appropriate material through an appropriate technique (sugar-coated tablet, film-coated tablet, etc.). Pelletizing may be performed by means of compression or another appropriate method for shaping into a certain form.

<5> A solid preparation produced by disposing component (A) and component (B) on different layers so that component (A) and component (B) are substantially in non-contact with each other to thereby provide a multilayer tablet, and optionally coating the multilayer tablet with an appropriate material through an appropriate technique (sugar-coated tablet, film-coated tablet, etc.). The multilayer tablet is preferably a multilayer tablet having three or more layers in which an component (A)-containing layer and an component (B)-containing layer are in non-contact with each other. The powdered product, granulated product, etc. produced in <1> or <2> may be used as component (A) and component (B).

<6> A solid preparation produced by disposing any one of component (A) and component (B) on a center tablet (also referred to as a core tablet or nucleus tablet) so that component (A) and component (B) are substantially in non-contact with each other to thereby provide a dry coated tablet, and optionally coating the dry coated tablet with an appropriate material through an appropriate technique (sugar-coated tablet, film-coated tablet, etc.). The powdered product, granulated product, etc. produced in <1> or <2> may be used as component (A) and component (B).

<7> A solid preparation produced through the method according to one of <1> to <4> or <6> using an inclusion compound formed by clathrating any one or both of component (A) and component (B) with a cyclodextrin species such as α-cyclodextrin, β-cyclodextrin or γ-cyclodextrin, instead of a powdered product, granulated product, etc. produced in the method in <1> or <2>.

<8> A solid preparation produced by incorporating any one of component (A) and component (B) into a preparation produced through a conventional method, providing the preparation with a sugar coating layer or film coating layer, and incorporating the counterpart into the sugar coating layer or film coating layer so that component (A) and component (B) are substantially in non-contact with each other (sugar-coated tablet, film-coated tablet, etc. when the dosage form is a tablet).

The powdered product or granulated product in <1>, <2>, etc. may be produced through a known dry or wet granulation method such as extrusion granulation, tumbling granulation, agitation granulation, fluidized bed granulation, spray dry granulation, crushing granulation, or melt granulation, by use of additives for pharmaceutical preparation in accordance with needs. The powdered product or granulated product containing component (A) and the powdered product or granulated product containing component (B) may be produced through the same granulation method, or through different granulation methods.

From the viewpoint of suppressing the interaction and the viewpoint of ease of production, the pharmaceutical composition is preferably the solid preparation in the aforementioned aspect <8>, more preferably a solid preparation produced by incorporating pemafibrate, a salt thereof or a solvate thereof into a preparation produced through a conventional method, providing the surface of the preparation with a layer (sugar coating layer or film coating layer), and incorporating component (B) into the layer, particularly preferably a film-coated tablet containing pemafibrate, a salt thereof or a solvate thereof in a center tablet, and containing component (B) in a coating layer.

The pharmaceutical composition of the present invention can be produced through a known method depending on its dosage form.

For example, the pharmaceutical composition, when it is a solid preparation, can be produced through appropriate combination of unit operations such as grinding, mixing, granulation, drying, grain size adjustment, classification, filling, pelletizing and coating.

More specifically, for example, when the dosage form of the pharmaceutical composition is a granular preparation such as a granule, a powder or a pill, additives for pharmaceutical preparation such as diluents, binders, disintegrants and lubricants are used, and after mixing these components in accordance with needs, the mixture is granulated through a known granulation method such as extrusion granulation, tumbling granulation, agitation granulation, fluidized bed granulation, spray granulation, melt granulation or crushing granulation to obtain a granulated product, and the granulated product is subjected to classification, grain size adjustment and the like in accordance with needs, whereby the pharmaceutical composition can be produced. The obtained granulated product can be coated through a known method with a coating agent etc.

When the dosage form of the pharmaceutical composition is a tablet, appropriate additives for pharmaceutical preparation such as diluents, binders, disintegrants and lubricants are used in accordance with needs, and these components are mixed to obtain the mixture, which is then directly compressed (pelletized) (through a direct powder compression method), or compressed (pelletized) (through a semidry grain compression method, dry granule compression method, wet grain compression method or the like) after the aforementioned granulated product is subjected to classification, grain size adjustment and the like, whereby the pharmaceutical composition can be produced. The obtained compressed product (tablet) can be coated through a known method with a coating agent etc.

When the dosage form of the pharmaceutical composition is a capsule, the granulated product or compressed product may be capsulated.

Pharmaceutically acceptable carriers (additives for pharmaceutical preparation) may be added to the pharmaceutical composition depending on its dosage form. Examples of the additives for pharmaceutical preparation include, but are not limited to, diluents, disintegrants, binders, lubricants, plasticizers, film formers, poorly water-soluble polymer substances, antioxidants, flavors and sweetening agents. As specific examples of these additives for pharmaceutical preparation, those described in Japanese Pharmaceutical Excipients Directory 2016 (issued by Yakuji Hippo, Limited), Handbook of Pharmaceutical Excipients, Seventh Edition (issued by Pharmaceutical Press), etc. may be used.

Specific examples of the diluents include inorganic diluents such as anhydrous sodium sulfate, anhydrous dibasic calcium phosphate, sodium chloride, calcium sulfate, calcium monohydrogen phosphate, dibasic calcium phosphate, dibasic sodium phosphate, monobasic potassium phosphate, monobasic calcium phosphate and monobasic sodium phosphate; and organic diluents such as corn syrup solids, starch (wheat starch, rice starch, corn starch, partially pregelatinized starch, etc.), fructose, caramel, agar, xylitol, paraffin, crystalline cellulose, powdered cellulose, sucrose, maltose, lactose, lactose monohydrate, white soft sugar, glucose, pullulan, maltitol, reduced maltose starch syrup, powdery reduced maltose starch syrup, erythritol, sorbitol, mannitol, lactitol, trehalose, reduced palatinose, maltose, polyvinylacetal diethylaminoacetate and calcium citrate. These diluents may be used singly, or in combinations of two or more thereof.

The total content of the diluents is not particularly limited, and is preferably 20 to 99 mass %, more preferably 30 to 95 mass %, with respect to the total mass of the pharmaceutical composition.

When solid composition (I) and/or (II) contains diluents, the total content of the diluents is not particularly limited, and is preferably 20 to 99 mass %, more preferably 30 to 95 mass %, with respect to the total mass of the pharmaceutical composition.

Specific examples of the disintegrants include super-disintegrants such as carboxymethyl starch sodium, croscarmellose sodium and crospovidone, carmellose, carmellose calcium, starch, gelatin, sodium hydrogencarbonate, dextrin, dehydroacetic acid and salts thereof, and povidone. These disintegrants may be used singly, or in combinations of two or more thereof.

The total content of the disintegrants is not particularly limited, and is preferably 1 to 30 mass %, more preferably 2 to 20 mast,*, with respect to the total mass of the pharmaceutical composition.

When solid composition (I) and/or (III) contains disintegrants, the total content of the disintegrants is not particularly limited, and is preferably 1 to 30 mass %, more preferably 2 to 20 mass %, with respect to the total mass of the pharmaceutical composition.

Specific examples of the binders include methylcellulose, hydroxypropylcellulose, hypromellose, carmellose sodium, starch (wheat starch, rice starch, corn starch, partially pregelatinized starch, etc.), dextrin, pullulan, acacia, agar, gelatin, tragacanth, sodium alginate, povidone and polyvinyl alcohol. These binders may be used singly, or in combinations of two or more thereof.

The total content of the binders is not particularly limited, and is preferably 1 to 30 mass %, more preferably 2 to 20 mass %, with respect to the total mass of the pharmaceutical composition.

When solid composition (I) and/or (II) contains binders, the total content of the binders is not particularly limited, and is preferably 1 to 30 mass %, more preferably 2 to 20 mass %, with respect to the total mass of the pharmaceutical composition.

Specific examples of the lubricants include calcium stearate and magnesium stearate. These lubricants may be used singly, or in combinations of two or more thereof.

The total content of the lubricants is not particularly limited, and is preferably 0.01 to 15 mass %, more preferably 0.1 to 10 mass %, with respect to the total mass of the pharmaceutical composition.

When solid composition (I) and/or (II) contains lubricants, the total content of the lubricants is not particularly limited, and is preferably 0.01 to 15 masse, more preferably 0.1 to 10 mass %, with respect to the total mass of the pharmaceutical composition.

Specific examples of the plasticizers include glycerin and sorbitol. These plasticizers may be used singly, or in combinations of two or more thereof.

Specific examples of the film farmers include alkylcelluloses such as methylcellulose and ethylcellulose; alginic acid or salts thereof such as sodium alginate; carrageenan; carboxyalkylcelluloses such as carboxymethylcellulose sodium, carboxymethylcellulose calcium, carboxymethylcellulose potassium, carboxymethylcellulose and carboxymethylethylcellulose; xanthan gum; hydroxyalkylcelluloses such as hydroxymethylcellulose, hydroxyethylcellulose, hydroxypropylcellulose, hypromellose (hydroxypropylmethylcellulose); pullulan; and polyvinylpyrrolidone. One of these film formers or a combination of two or more of these film formers is preferable.

The total content of the film formers is preferably 1 to 10 mass, more preferably 3 to 5 mass %, with respect to the total mass of the pharmaceutical composition.

When solid composition (I) and/or (II) contains film formers, the total content of the film formers is preferably 1 to 10 mass %, more preferably 3 to 5 masse, with respect to the total mass of the pharmaceutical composition.

Specific examples of the poorly water-soluble polymer substances include carboxyvinyl polymers. These poorly water-soluble polymer substances may be used singly, or in combinations of two or more thereof.

Specific examples of the antioxidants include ascorbic acid, sodium hydrogen sulfite, sodium sulfite, sodium edetate, erythorbic acid, dibutylhydroxytoluene, natural vitamin E, tocopherol and butylhydroxyanisole. These antioxidants may be used singly, or in combinations of two or more thereof.

Specific examples of the flavors include terpenes such as limonene, pinene, camphene, cymene, cineole, citronellol, geraniol, nerol, linalool, menthol, terpineol, rhodinol, borneol, isoborneol, menthone, camphor, eugenol and cinnzeylanol; terpene-containing essential oils such as bitter orange oil, orange oil, peppermint oil, camphor white oil, *eucalyptus* oil, turpentine oil, lemon oil, ginger oil, clove oil, cinnamon oil, lavender oil, fennel oil, chamomile oil, fermented soybean oil and spearmint oil; and acidifiers such as ascorbic acid, tartaric acid, citric acid, malic acid and salts thereof. These flavors may be used singly, or in combinations of two or more thereof.

Examples of the sweetening agents include aspartame, *stevia*, sucralose, glycyrrhizic acid, thaumatin, acesulfame potassium, saccharin and saccharin sodium, and these sweetening agents may be used singly, or in combinations of two or more thereof.

The disease to which the pharmaceutical composition of the present invention is applied is not limited, and the pharmaceutical composition can be widely used for prevention or treatment of diseases against which administration of pemafibrate is known or expected to be effective.

For example, pemafibrate, a salt thereof or a solvate thereof has excellent PPAR-α agonist activity, and exhibits plasma triglyceride concentration reducing action, HDL cholesterol increasing action, etc. Therefore, the pharmaceutical composition of the present invention can be used preferably as an agent for prevention and/or treatment of dyslipidemia (hyperlipidemia, more specifically, for example primary hyperlipidemia and secondary hyperlipidemia), further preferably as an agent for prevention and/or treatment of hypertriglyceridemia, etc.

In addition, pemafibrate, a salt thereof or a solvate thereof is useful for prevention or treatment of NAFLD (non-alcoholic fatty liver disease). Therefore, the pharmaceutical composition of the present invention can also be used as an agent for prevention and/or treatment of NAFLD (more preferably NASH (non-alcoholic steatohepatitis)), etc.

Further, pemafibrate, a salt thereof or a solvate thereof may be used as an agent for treatment of primary biliary cirrhosis, etc.

The administration route of the pharmaceutical composition is not particularly limited, and can be determined in appropriate consideration of the target disease, the type of preparation, the sex, age, symptoms of a patient in need of the composition, and the like, but peroral administration is preferable from the viewpoint of ease of administration. The daily dose of the pharmaceutical composition can be taken as a single dose, or can be divided into 2 to 4 daily administrations, and taken before each meal, between meals, after each meal, before bedtime, or the like.

For example, the following aspects are disclosed herein and should not be construed as limiting the present invention.

[1-1] A pharmaceutical composition comprising the following components (A) and (B):

(A) pemafibrate, a salt thereof or a solvate thereof; and (B) one or more selected from the group consisting of the following components (B-1) to (B-4):

(B-1) a metal oxide;

(B-2) a dihydric alcohol;

(B-3) an ester species; and (B-4) a silicic acid compound, wherein component (A) and component (B) are substantially in non-contact with each other.

[1-2] The pharmaceutical composition according to [1-1], wherein in addition to components (A) and (B), other components are co-present in the pharmaceutical composition, and by the other components, contact between components (A) and (B) is substantially avoided.

[1-3] The pharmaceutical composition according to [1-1] or [1-2], wherein the pharmaceutical composition is a solid preparation.

[1-4] The pharmaceutical composition according to any one of [1-1] to [1-3], wherein the pharmaceutical composition is a solid preparation containing the following (I) and (II):

(I) component (A) itself or a solid composition containing component (A); and (II) component (B) itself or a solid composition containing component (B), with components (A) and (B) being substantially in non-contact with each other (except for the case where (I) is component (A) itself and (II) is component (B) itself).

[1-5] The pharmaceutical composition according to any one of [1-1] to [1-4], wherein the pharmaceutical composition is in the form of a solid preparation selected from the group consisting of the aforementioned aspects <1> to <8>.

[1-6] A film-coated tablet comprising a center tablet and a film coating layer, the center tablet containing pemafibrate, a salt thereof or a solvate thereof, the film coating layer containing one or more selected from the group consisting of a metal oxide (component (B-1)), a dihydric alcohol (component (B-2)), an ester species (component (B-3)) and a silicic acid compound (component (B-4)).

[1-7] The pharmaceutical composition according to any one of [1-1] to [1-6], wherein component (B-1) is one or more selected from the group consisting of yellow oxide of iron, yellow ferric oxide, brown iron oxide, black iron oxide, synthetic hydrotalcite, zinc oxide, aluminum oxide, calcium oxide, titanium oxide and magnesium oxide and red ferric oxide.

[1-8] The pharmaceutical composition according to any one of [1-1] to [1-7], wherein component (B-2) is one or more selected from the group consisting of ethylene glycol, propylene glycol, 1,3-propanediol, 2-methyl-1,3-propanediol, 1,3-butanediol, diethylene glycol, dipropylene glycol, macrogol (polyethylene glycol), polypropylene glycol and polyoxyethylene polyoxypropylene glycol.

[1-9] The pharmaceutical composition according to any one of [1-1] to [1-8], wherein component (B-3) is one or more selected from the group consisting of acetyltriethyl citrate, acetyltributyl citrate, triethyl citrate, tributyl citrate and triacetin.

[1-10] The pharmaceutical composition according to any one of [1-1] to [1-9], wherein component (B-4) is one or more selected from the group consisting of magnesium aluminosilicate, calcium silicate, magnesium silicate, aluminum magnesium silicate, light anhydrous silicic acid and heavy anhydrous silicic acid.

[1-11] The pharmaceutical composition according to any one of [1-1] to [1-10], wherein the dosage form thereof is a tablet, a capsule, a granule, a powder or a pill.

[1-12] The pharmaceutical composition according to any one of [1-1] to [1-11], wherein the pharmaceutical composition is an agent for prevention and/or treatment of a disease selected from dyslipidemia (hyperlipidemia, more specifically, for example primary hyperlipidemia and secondary hyperlipidemia), HAM (more preferably NASH (non-alcoholic steatohepatitis)) and primary biliary cirrhosis.

[2-1] A pharmaceutical composition comprising the following components (A) and (B-1);

(A) pemafibrate, a salt thereof or a solvate thereof; and (B-1) a metal oxide, wherein component (A) and component (B-1) are substantially in non-contact with each other.

[2-2] The pharmaceutical composition according to [2-1], wherein in addition to components (A) and (B-1), other components are co-present in the pharmaceutical composition, and by the other components, contact between components (A) and (B-1) is substantially avoided.

[2-3] The pharmaceutical composition according to [2-1] or [2-2], wherein the pharmaceutical composition is a solid preparation.

[2-4] The pharmaceutical composition according to any one of [2-1] to [2-3], wherein the pharmaceutical composition is a solid preparation containing the following (I) and (II):

(I) component (A) itself or a solid composition containing component (A); and (II) component (B-1) itself or a solid composition containing component (B-1), with components (A) and (B-1) being substantially in non-contact with each other (except for the case where (I) is component (A) itself and (II) is component (B-1) itself).

[2-5] The pharmaceutical composition according to any one of [2-1] to [2-4], wherein the pharmaceutical composition is in the form of a solid preparation selected from the group consisting of the aforementioned aspects <1> to <8> (where "component (B)" is replaced by "component (B-1)").

[2-6] A film-coated tablet comprising a center tablet and a film coating layer, the center tablet containing pemafibrate, a salt thereof or a solvate thereof, the film coating layer containing a metal oxide (component (B-1)).

[2-7] The pharmaceutical composition according to any one of [2-1] to [2-6], wherein component (B-1) is one or more selected from the group consisting of yellow oxide of iron, yellow ferric oxide, brown iron oxide, black iron oxide, synthetic hydrotalcite, zinc oxide, aluminum oxide, calcium oxide, titanium oxide and magnesium oxide and red ferric oxide.

[2-8] The pharmaceutical composition according to any one of [2-1] to [2-7], wherein component (B-1) is one or more selected from the group consisting of synthetic hydrotalcite, iron oxide, magnesium oxide, yellow ferric oxide, brown iron oxide, black iron oxide, titanium oxide and red ferric oxide.

[2-9] The pharmaceutical composition according to any one of [2-1] to [2-8], wherein component (B-1) is titanium oxide.

[2-10] The pharmaceutical composition according to any one of [2-1] to [2-9], wherein the dosage form thereof is a tablet, a capsule, a granule, a powder or a pill.

[2-11] The pharmaceutical composition according to any one of [2-1] to [2-10], wherein the pharmaceutical composition is an agent for prevention and/or treatment of a disease selected from dyslipidemia (hyperlipidemia, more specifically, for example primary hyperlipidemia and secondary hyperlipidemia), NAFLD (more preferably NASH (non-alcoholic steatohepatitis)) and primary biliary cirrhosis.

[3-1] A pharmaceutical composition comprising the following components (A) and (B-2).

(A) pemafibrate, a salt thereof or a solvate thereof; and (B-2) a dihydric alcohol, wherein component (A) and component (B-2) are substantially in non-contact with each other.

[3-2] The pharmaceutical composition according to [3-1], wherein in addition to components (A) and (B-2), other components are co-present in the pharmaceutical composition, and by the other components, contact between components (A) and (B-2) is substantially avoided.

[3-3] The pharmaceutical composition according to [3-1] or [3-2], wherein the pharmaceutical composition is a solid preparation.

[3-4] The pharmaceutical composition according to any one of [3-1] to [3-3], wherein the pharmaceutical composition is a solid preparation containing the following (I) and (II):

(I) component (A) itself or a solid composition containing component (A); and (II) component (8-2) itself or a solid composition containing component (8-2), with components (A) and (B-2) being substantially in non-contact with each other (except for the case where (I) is component (A) itself and (II) is component (B-2) itself).

[3-5] The pharmaceutical composition according to any one of [3-1] to [3-4], wherein the pharmaceutical composition is in the form of a solid preparation selected from the group consisting of the aforementioned aspects <1> to <8> (where "component (B)" is replaced by "component (B-2)").

[3-6] A film-coated tablet comprising a center tablet and a film coating layer, the center tablet containing pemafibrate, a salt thereof or a solvate thereof, the film coating layer containing a dihydric alcohol (component (B-2)).

[3-7] The pharmaceutical composition according to any one of [3-1] to [3-6], wherein component (B-2) is one or more selected from the group consisting of ethylene glycol, propylene glycol, 1,3-propanediol, 2-methyl-1,3-propanediol, 1,3-butanediol, diethylene glycol, dipropylene glycol, macrogol (polyethylene glycol), polypropylene glycol and polyoxyethylene polyoxypropylene glycol.

[3-8] The pharmaceutical composition according to any one of [3-1] to [3-7], wherein component. (B-2) is one or more selected from the group consisting of macrogol 100, macrogol 200, macrogol 300, macrogol 400, macrogol 600, macrogol 1000, macrogol 1500, macrogol 1540, macrogol 4000, macrogol 6000, macrogol 20000 and macrogol 35000.

[3-9] The pharmaceutical composition according to any one of [3-1] to [3-8], wherein component (B-2) is macrogol 6000.

[3-10] The pharmaceutical composition according to any one of [3-1] to [3-9], wherein the dosage form thereof is a tablet, a capsule, a granule, a powder or a pill.

[3-11] The pharmaceutical composition according to any one of [3-1] to [3-10], wherein the pharmaceutical composition is an agent for prevention and/or treatment of a disease selected from dyslipidemia (hyperlipidemia, more specifically, for example primary hyperlipidemia and secondary hyperlipidemia), NAFLD (more preferably NASH (non-alcoholic steatohepatitis)) and primary biliary cirrhosis.

[4-1] A pharmaceutical composition comprising the following components (A) and (B-3):

(A) pemafibrate, a salt thereof or a solvate thereof; and (B-3) an ester species, wherein component (A) and component (B-3) are substantially in non-contact with each other.

[4-2] The pharmaceutical composition according to [4-1], wherein in addition to components (A) and (B-3), other components are co-present in the pharmaceutical composition, and by the other components, contact between components (A) and (B-3) is substantially avoided.

[4-3] The pharmaceutical composition according to [4-1] or [4-2], wherein the pharmaceutical composition is a solid preparation.

[4-4] The pharmaceutical composition according to any one of [4-1] to [4-3], wherein the pharmaceutical composition is a solid preparation containing the following (I) and (II):

(I) component (A) itself or a solid composition containing component (A); and (II) component (B-3) itself or a solid composition containing component (B-3), with components (A) and (B-3) being substantially in non-contact with each other (except for the case where (I) is component (A) itself and (II) is component (B-3) itself).

[4-5] The pharmaceutical composition according to any one of [4-1] to [4-4], wherein the pharmaceutical composition is in the form of a solid preparation selected from the group consisting of the aforementioned aspects <1> to <8> (where "component (B)" is replaced by "component (B-3)").

[4-6] A film-coated tablet comprising a center tablet and a film coating layer, the center tablet containing pemafibrate, a salt thereof or a solvate thereof, the film coating layer containing an ester species (component (B-3)).

[4-7] The pharmaceutical composition according to any one of [4-1] to [4-6], wherein component (B-3) is one or more selected from the group consisting of acetyltriethyl citrate, acetyltributyl citrate, triethyl citrate, tributyl citrate and triacetin.

[4-8] The pharmaceutical composition according to any one of [4-1] to [4-7], wherein component (B-3) is one or more selected from the group consisting of triethyl citrate and triacetin.

[4-9] The pharmaceutical composition according to any one of [4-1] to [4-8], wherein component (B-3) is triethyl citrate.

[4-10] The pharmaceutical composition according to any one of [4-1] to [4-9], wherein the dosage form thereof is a tablet, a capsule, a granule, a powder or a pill.

[4-11] The pharmaceutical composition according to any one of [4-1] to [4-10], wherein the pharmaceutical composition is an agent for prevention and/or treatment of a disease selected from dyslipidemia (hyperlipidemia, more specifically, for example primary hyperlipidemia and secondary hyperlipidemia), NAFLD (more preferably NASH (non-alcoholic steatohepatitis)) and primary biliary cirrhosis.

[5-1] A pharmaceutical composition comprising the following components (A) and (B-4):

(A) pemafibrate, a salt thereof or a solvate thereof; and (B-4) a silicic acid compound, wherein component 0%) and component (B-4) are substantially in non-contact with each other.

[5-2] The pharmaceutical composition according to [5-1], wherein in addition to components (A) and (B-4), other components are co-present in the pharmaceutical composition, and by the other components, contact between components (A) and (B-4) is substantially avoided.

[5-3] The pharmaceutical composition according to [5-1] or [5-2], wherein the pharmaceutical composition is a solid preparation.

[5-4] The pharmaceutical composition according to any one of [5-1] to [5-3], wherein the pharmaceutical composition is a solid preparation containing the following (I) and (II):

(I) component (A) itself or a solid composition containing component (A); and (II) component (B-4) itself or a solid composition containing component (B-4), with components (A) and (B-4) being substantially in non-contact with each other (except for the case where (I) is component (A) itself and (II) is component (B-4) itself).

[5-5] The pharmaceutical composition according to any one of [5-1] to [5-4], wherein the pharmaceutical composition is in the form of a solid preparation selected from the group consisting of the aforementioned aspects <1> to <8> (where "component (B)" is replaced by "component. (B-4)").

[5-6] A film-coated tablet comprising a center tablet and a film coating layer, the center tablet containing pemafibrate, a salt thereof or a solvate thereof, the film coating layer containing a silicic acid compound (component (B-4)).

[5-7] The pharmaceutical composition according to any one of [5-1] to [5-6], wherein component (B-4) is one or more selected from the group consisting of magnesium aluminosilicate, calcium silicate, magnesium silicate, aluminum magnesium silicate, light anhydrous silicic acid and heavy anhydrous silicic acid.

[5-8] The pharmaceutical composition according to any one of [5-1] to [5-7], wherein component (B-4) is one or more selected from the group consisting of light anhydrous silicic acid and heavy anhydrous silicic acid.

[5-9] The pharmaceutical composition according to any one of [5-1] to [5-8], wherein component (B-4) is light anhydrous silicic acid.

[5-10] The pharmaceutical composition according to any one of [5-1] to [5-9], wherein the dosage form thereof is a tablet, a capsule, a granule, a powder or a pill.

[5-11] The pharmaceutical composition according to any one of [5-1] to [5-10], wherein the pharmaceutical composition is an agent for prevention and/or treatment of a disease selected from dyslipidemia (hyperlipidemia, more specifically, for example primary hyperlipidemia and secondary hyperlipidemia), NAFLD (more preferably NASH (non-alcoholic steatohepatitis)) and primary biliary cirrhosis.

[6-1] A method for producing a pharmaceutical composition, the method comprising the step of incorporating the following components (A) and (B):

(A) pemafibrate, a salt thereof or a solvate thereof; and (B) one or more selected from the group consisting of the following components (B-1) to (B-4):

(B-1) a metal oxide;

(B-2) a dihydric alcohol;

(B-3) an ester species; and (B-4) a silicic acid compound, wherein component (A) and component (B) are substantially in non-contact with each other.

[6-2] The method according to [6-1], wherein in addition to components (A) and (B), other components are co-present in the pharmaceutical composition, and by the other components, contact between components (A) and (B) is substantially avoided.

[6-3] The method according to [6-1] or [6-2], wherein the pharmaceutical composition is a solid preparation.

[6-4] The method according to any one of [6-1] to [6-3], wherein the pharmaceutical composition is a solid preparation containing the following (I) and (II):

(I) component (A) itself or a solid composition containing component (A); and (II) component (B) itself or a solid composition containing component (B), with components (A) and (B) being substantially in non-contact with each other (except for the case where (I) is component (A) itself and (II) is component (B) itself).

[6-5] The method according to any one of [6-1] to [6-4], wherein the pharmaceutical composition is in the form of a solid preparation selected from the group consisting of the aforementioned aspects <1> to <8>.

[6-6] The method according to any one of [6-1] to [6-5], wherein the pharmaceutical composition is in the form of a film-coated tablet including a center tablet and a film coating layer, the center tablet containing pemafibrate, a salt thereof or a solvate thereof, the film coating layer containing one or more selected from the group consisting of a metal oxide (component (B-1)), a dihydric alcohol (component (B-2)), an ester species (component (B-3)) and a silicic acid compound (component (B-4)).

[6-7] The method according to any one of [6-1] to [6-6], wherein component (B-1) is one or more selected from the group consisting of yellow oxide of iron, yellow ferric oxide, brown iron oxide, black iron oxide, synthetic hydrotalcite, zinc oxide, aluminum oxide, calcium oxide, titanium oxide and magnesium oxide and red ferric oxide.

[6-8] The method according to any one of [6-1] to [6-7], wherein component (B-2) is one or more selected from the group consisting of ethylene glycol, propylene glycol, 1,3-propanediol, 2-methyl-1,3-propanediol, 1,3-butanediol, diethylene glycol, dipropylene glycol, macrogol (polyethylene glycol), polypropylene glycol and polyoxyethylene polyoxypropylene glycol.

[6-9] The method according to any one of [6-1] to [6-9], wherein component (B-3) is one or more selected from the group consisting of acetyltriethyl citrate, acetyltributyl citrate, triethyl citrate, tributyl citrate and triacetin.

[6-10] The method according to any one of [6-1] to [6-9], wherein component (B-4) is one or more selected from the group consisting of magnesium aluminosilicate, calcium silicate, magnesium silicate, aluminum magnesium silicate, light anhydrous silicic acid and heavy anhydrous silicic acid.

[6-11] The method according to any one of [6-1] to [6-10], wherein the dosage form of the pharmaceutical composition is a tablet, a capsule, a granule, a powder or a pill.

[6-12] The method according to any one of [6-1] to [6-11], wherein the pharmaceutical composition is an agent for prevention and/or treatment of a disease selected from dyslipidemia (hyperlipidemia, more specifically, for example primary hyperlipidemia and secondary hyperlipidemia), NAFLD (more preferably NASH (non alcoholic steatohepatitis)) and primary biliary cirrhosis.

[7-1] A method for stabilizing pemafibrate, the method comprising the step of incorporating the following components (A) and (B):

(A) pemafibrate, a salt thereof or a solvate thereof; and (B) one or more selected from the group consisting of the following components (B-1) to (B-4):

(B-1) a metal oxide;

(B-2) a dihydric alcohol;

(B-3) an ester species; and (B-4) a silicic acid compound, wherein component (A) and component (B) are substantially in non-contact with each other.

[7-2] The method according to [7-1], wherein in addition to components (A) and (B), other components are co-present in the pharmaceutical composition, and by the other components, contact between components (A) and (B) is substantially avoided.

[7-3] The method according to [7-1] or [7-2], wherein the pharmaceutical composition is a solid preparation.

[7-4] The method according to any one of [7-1] to [7-3], wherein the pharmaceutical composition is a solid preparation containing the following (I) and (II):

(I) component (A) itself or a solid composition containing component (A); and (II) component (B) itself or a solid composition containing component (B), with components (A) and (B) being substantially in non-contact with each other (except for the case where (I) is component (A) itself and (II) is component (B) itself).

[7-5] The method according to any one of [7-1] to [7-4], wherein the pharmaceutical composition is in the form of a solid preparation selected from the group consisting of the aforementioned aspects <1> to <8>.

[7-6] The method according to any one of [7-1] to [7-5], wherein the pharmaceutical composition is in the form of a film-coated tablet including a center tablet and a film coating layer, the center tablet containing pemafibrate, a salt thereof or a solvate thereof, the film coating layer containing one or more selected from the group consisting of a metal oxide (component (B-1)), a dihydric alcohol (component (B-2)), an ester species (component (B-3)) and a silicic acid compound (component (B-4)).

[7-7] The method according to any one of [7-1] to [7-6], wherein component (B-1) is one or more selected from the group consisting of yellow oxide of iron, yellow ferric oxide, brown iron oxide, black iron oxide, synthetic hydrotalcite, zinc oxide, aluminum oxide, calcium oxide, titanium oxide and magnesium oxide and red ferric oxide.

[7-8] The method according to any one of [7-1] to [7-7], wherein component (B-2) is one or more selected from the group consisting of ethylene glycol, propylene glycol, 1,3-propanediol, 2-methyl-1,3-propanediol, 1,3-butanediol, diethylene glycol, dipropylene glycol, macrogol (polyethylene glycol), polypropylene glycol and polyoxyethylene polyoxypropylene glycol.

[7-9] The method according to any one of [7-1] to [7-8], wherein component (B-3) is one or more selected from the group consisting of acetyltriethyl citrate, acetyltributyl citrate, triethyl citrate, tributyl citrate and triacetin.

[7-10] The method according to any one of [7-1] to [7-9], wherein component (B-4) is one or more selected from the group consisting of magnesium aluminosilicate, calcium silicate, magnesium silicate, aluminum magnesium silicate, light anhydrous silicic acid and heavy anhydrous silicic acid.

[7-11] The method according to any one of [7-1] to [7-10], wherein the dosage form of the pharmaceutical composition is a tablet, a capsule, a granule, a powder or a pill.

[7-12] The method according to any one of [7-1] to [7-11], wherein the pharmaceutical composition is an agent for prevention and/or treatment of a disease selected from dyslipidemia (hyperlipidemia, more specifically, for example primary hyperlipidemia and secondary hyperlipidemia), NAFLD (more preferably NASH (non alcoholic steatohepatitis)) and primary biliary cirrhosis.

EXAMPLES

The present invention will next be described in detail by way of Examples, which should not be construed as limiting the invention thereto.

In Test Examples below, measurement was performed through HPLC using an ODS column as a column and an ultraviolet spectrophotometer as a detector.

Test Example 1

Examination of Storage Stability of Pemafibrate 250 mg of pemafibrate was encapsulated in a polypropylene container (tight container defined in The Japanese Pharmacopoeia, 17th Edition, General Rules), and stored in a dark place at a temperature of 60° C. for 1 month.

The amounts of pemafibrate-derived decomposition products (related substances) before the start of storage and after storage at 60° C. for 1 month were evaluated through the following method.

The sum of related substance-derived peak areas was evaluated in terms of a ratio (%) to the pemafibrate-derived peak area using an HPLC apparatus, and the ratio was defined as the "Total amount (%) of related substances".

Table 1 shows the results.

TABLE 1

| | Total amount (%) of related substances | |
|---|---|---|
| | Before storage | After storage at 60° C. for 1 month |
| Pemafibrate alone | <0.05 | <0.05 |

As shown in Table 1, pemafibrate alone was stable, and there was no substantive increase in the amount of related substances even after storage at 60° C. for 1 month.

Test Example 2

Interaction Study 250 mg of each of the samples of Reference Examples 1 to 4 shown below was encapsulated in a polypropylene container (tight container defined in The Japanese Pharmacopoeia, 17th Edition, General Rules), and stored in a dark place at a temperature of 60° C. for 1 month.

Reference Example 1

1 part by mass of titanium oxide (Titanium Oxide NA-65: Toho Titanium Co., Ltd.) was mixed with 1 part by mass of pemafibrate to prepare the sample of Reference Example 1.

Reference Example 2

1 part by mass of macrogol 6000 (Macrogol 6000: NOF CORPORATION) was mixed with 1 part by mass of pemafibrate to prepare the sample of Reference Example 2.

Reference Example 3

1 part by mass of triethyl citrate (CITROFLEX 2: MORIMURA BROS., INC.) was mixed with 1 part by mass of pemafibrate to prepare the sample of Reference Example 3.

Reference Example 4

10 parts by mass of light anhydrous silicic acid (AEROSIL 300: NIPPON AEROSIL CO., LTD.) was mixed with 1 part by mass of pemafibrate to prepare the sample of Reference Example 4.

Pemafibrate-derived decomposition products (related substances) in the samples were examined in the following manner.

The total amounts (U) of pemafibrate-derived related substances before the start of storage and after storage at 60° C. for 1 month in each of Reference Examples 1 to 4 were measured using an HPLC apparatus through the same method as in Test Example 1.

From the thus-obtained total amounts (%) of pemafibrate-derived related substances before the start of storage and after storage at 60° C. for 1 month in each of Reference Examples 1 to 4, an increase (%) in the amount of related substances was calculated in accordance with the following equation.

Increase (%) in the amount of related substances=(total amount (%) of pemafibrate-derived related substances after storage at 60° C. for 1 month)−(total amount (%) of pemafibrate-derived related substances before start of storage).

Table 2 shows the results.

TABLE 2

| | Increase (%) in the amount of related substances |
|---|---|
| [Reference Example 1] pemafibrate + titanium oxide | 0.57 |
| [Reference Example 2] pemafibrate + macrogol 6000 | 1.16 |
| [Reference Example 3] pemafibrate + triethyl citrate | 0.97 |

TABLE 2-continued

| | Increase (%) in the amount of related substances |
|---|---|
| [Reference Example 1] pemafibrate + light anhydrous silicic acid | 0.26 |

When pemafibrate and titanium oxide (Reference Example 1), macrogol 6000 (Reference Example 2), triethyl citrate (Reference Example 3) or light anhydrous silicic acid (Reference Example 4) were mixed together, and stored at 60° C. for 1 month, there was an increase in the amount of pemafibrate-derived decomposition products (related substances) after storage as shown in Table 2. Particularly in Reference Examples 1 to 3, there was a marked increase in the amount of decomposition products. In contrast, when pemafibrate was stored alone, there was no substantive increase in the amount of related substances after storage at 60° C. for 1 month as shown in Test Example 1.

Thus, it was found that contact between pemafibrate, a salt thereof or a solvate thereof and one or more selected from the group consisting of a metal oxide typified by titanium oxide, a dihydric alcohol typified by macrogol 6000, an ester species typified by triethyl citrate and a silicic acid compound typified by light anhydrous silicic acid caused interaction, so that the amount of pemafibrate-derived decomposition products increased, and thus when these components are blended together to obtain a pharmaceutical composition, leading to development of a problem with storage stability.

Test Example 3

Interaction Study 250 mg of each of the samples of Control 1 and Reference Examples 5 to 7 shown below was encapsulated in a polypropylene container (tight container defined in The Japanese Pharmacopoeia, 17th Edition, General Rules), and stored in a dark place at a temperature of 60° C. for 2 weeks.

<Control 1>

Pemafibrate was defined as the sample of Control 1.

Reference Example 5

1 part by mass of macrogol 6000 (Macrogol 6000: NOF CORPORATION) was mixed with 1 part by mass of pemafibrate to prepare the sample of Reference Example 5.

Reference Example 6

10 parts by mass of macrogol 400 (Macrogol 400: NOF CORPORATION) was mixed with 1 part by mass of pemafibrate to prepare the sample of Reference Example 6.

Reference Example 7

10 parts by mass of propylene glycol was mixed with 1 part by mass of pemafibrate to prepare the sample of Reference Example 7.

The states (the presence or absence of discoloration) of the samples before the start of storage and after storage at 60°G for 2 weeks were visually examined.

Table 3 shows the results.

TABLE 3

| | State | |
|---|---|---|
| | Before storage | After storage at 60° C. for 2 weeks |
| [Control 1] pemafibrate alone | White | White |
| [Reference Example 5] pemafibrate + macrogol 6000 | White | Changed to pale yellow |
| [Reference Example 6] pemafibrate + macrogol 400 | White | Changed to yellow |
| [Reference Example 7] pemafibrate + propylene glycol | White | Changed to yellow |

As shown in Table 3, discoloration did not occur when pemafibrate was stored alone at 60° C. for 2 weeks, whereas a color change to pale yellow or yellow occurred when pemafibrate was mixed with macrogol 6000 (Reference Example 5), macrogol 400 (Reference Example 6) or propylene glycol (Reference Example 7), and the mixture was store at 60° C. for 2 weeks. These results indicate that when instead of macrogol 6000, a dihydric alcohol other than macrogol 6000, such as macrogol 400 or propylene glycol, is mixed with pemafibrate, the same change upon blending occurs as in the case where macrogol 6000 is used.

Test Example 4

Study on Interaction Suppressing Means

On the basis of the results of Test Example 2 and Test Example 3, which reveals that contact between pemafibrate, a salt thereof or a solvate thereof and one or more selected from the group consisting of a metal oxide, a dihydric alcohol, an ester species and a silicic acid compound causes an interaction, the present inventor prepared a pharmaceutical composition containing pemafibrate, a salt thereof or a solvate thereof and one or more selected from the group consisting of a metal oxide, a dihydric alcohol, an ester species and a silicic acid compound, with both the components being substantially in non-contact with each other for preventing contact between the components.

A solid preparation (film-coated tablet: Example 1) containing pemafibrate in a solid preparation (core tablet) and having, on the surface of the solid preparation, a layer (film coating layer) containing titanium oxide, triethyl citrate and light anhydrous silicic acid was produced in accordance with the following method, and packed in a PTP (tight container defined in The Japanese Pharmacopoeia, 17th Edition, General Rules), and the PTP was further packed in an aluminum bag (tight container defined in The Japanese Pharmacopoeia, 17th Edition, General Rules), and stored in a dark place at a temperature of 60° C. for 1 month.

Example 1

50 parts by mass of pemafibrate, 874 parts by mass of lactose monohydrate, 24 parts by mass of croscarmellose sodium, 240 parts by mass of microcrystalline cellulose and 12 parts by mass of magnesium stearate were mixed together, and then compressed to obtain core tablets containing 5 mg of pemafibrate per tablet (120 mg).

Next, 6 parts by mass of titanium oxide (Toho Titanium Co., Ltd.), 12 parts by mass of triethyl citrate (MORIMURA BROS., INC.), 46 parts by mass of hypromellose and 6 parts by mass of light anhydrous silicic acid (NIPPON AEROSIL CO., LTD.) were dissolved/dispersed in purified water to obtain a film coating solution. The core tablet was coated with the film coating solution using a ventilation-type coater, and 0.06 parts by mass of carnauba wax was added to polish the tablet. Accordingly, film-coated tablets each having a weight of 127 mg was obtained.

Pemafibrate-derived decomposition products (related substances) in the film-coated tablet obtained through the aforementioned method were examined in the following manner.

The increase (%) in the amount of pemafibrate-derived related substances after storage at 60° C. for 1 month was examined using an HPLC apparatus through the same method as in Test Example 2.

Table 4 shows the results.

TABLE 4

| | Increase (%) in the amount of related substances |
|---|---|
| [Example 1]<br>Core tablet: containing pemafibrate<br>Film coating layer: containing titanium oxide, triethyl citrate and light anhydrous silicic acid | 0.03 |

Table 4 reveals that by blending titanium oxide, triethyl citrate and light anhydrous silicic acid in a film coating layer to prevent these components from contacting pemafibrate (blended in the core tablet), the interaction is suppressed to inhibit increase in the amount of related substances (Example 1)

The results of Test Examples 1 to 4 reveal that in a pharmaceutical composition containing pemafibrate, a salt thereof or a solvate thereof and one or more selected from the group consisting of a metal oxide, a dihydric alcohol, an ester species and a silicic acid compound, with the components being substantially in non-contact with each other, pemafibrate can be stabilized.

Production Examples 1 to 12

Film coating layers containing the components in the amounts (mg) thereof per tablet shown in Tables 5 and 6 are conventionally stacked on the surfaces of the center tablets produced in Example 1, whereby the film-coated tablets of Production Examples 1 to 12, respectively, can be produced.

TABLE 5

| | Production Example 1 | Production Example 2 | Production Example 3 | Production Example 4 | Production Example 5 | Production Example 6 |
|---|---|---|---|---|---|---|
| Titanium oxide | 0.7 | 0.9 | 2 | | 0.3 | |
| Yellow ferric oxide | 0.1 | | | | | |
| Red ferric oxide | | 0.1 | | | | |
| Magnesium oxide | | | 0.4 | | | |
| Black iron oxide | | | 0.1 | | | |
| Macrogol 400 | 0.2 | | | | 0.1 | |
| Macrogol 6000 | | 0.2 | | 0.3 | 0.3 | |
| Propylene glycol | | 0.1 | | | | |
| Polyoxyethylene polyoxypropylene glycol | | | 0.5 | | | |
| Ethylene glycol | | | | | 0.1 | 0.1 |
| Polysorbate 80 | | | 0.5 | | | |
| Triacetin | | 0.2 | | | | |
| Trethyl citrate | | | | 0.2 | | 0.4 |
| Light anhydride silicic acid | | | | 0.4 | | 0.3 |
| Talc | | | | 0.4 | 0.2 | |
| Silicon dioxide | | | | | | 0.2 |
| Hydrated silicon dioxide | | | | 0.2 | | |
| Magnesium aluminosilicate | | | | | 0.5 | |
| Hypromellose | 2 | 3.3 | 3.5 | | | |
| Hydroxypropylcellulose | | | | 1.5 | 3.5 | 6 |
| Coating amount | 3 mg | 5 mg | 7 mg | 3 mg | 5 mg | 7 mg |

TABLE 6

| | Production Example 7 | Production Example 8 | Production Example 9 | Production Example 10 | Production Example 11 | Production Example 12 |
|---|---|---|---|---|---|---|
| Yellow oxide of iron | 0.7 | 0.9 | 2 | | | |
| Brown iron oxide | 0.1 | | | | | |
| Synthetic hydrotalcite | | 0.1 | | | | |
| Zinc oxide | | | 0.2 | | | |
| Aluminum oxide | | | 0.1 | | | |
| Calcium oxide | | | 0.2 | | | |
| 1,3-Propanediol | 0.2 | | | | | |
| 2-Methyl-1,3-propanediol | | 0.2 | | | | |

TABLE 6-continued

| | Production Example 7 | Production Example 8 | Production Example 9 | Production Example 10 | Production Example 11 | Production Example 12 |
|---|---|---|---|---|---|---|
| 3-Butandiol | | 0.1 | | | | |
| Diethylene glycol | | | 0.5 | | 0.3 | |
| Dipropylene glycol | | | | | | 0.1 |
| Propylene glycol | | | 0.5 | | | |
| Acetyltriethyl citrate | | 0.2 | | 0.3 | | |
| Acetyltributyl citrate | | | | | 0.1 | |
| Tributyl citrate | | | | 0.2 | | 0.3 |
| Calcium Silicate | | | | 0.4 | | 0.3 |
| Magnesium silicate | | | | 0.4 | 0.2 | |
| Aluminum magnesium silicate | | | | | | 0.2 |
| Heavy anhydrous silicic acid | | | | 0.2 | | |
| Hydrous amorphous silicon oxide | | | | | 0.5 | |
| Magnesium alumino-metasilicate | | | | | 0.3 | |
| Natural aluminum silicate | | | | | | 0.1 |
| Diatomaceous earth | | | | | 0.1 | |
| Kaolin | | 0.2 | | | | |
| Hypromellose | 2 | 3.3 | 3.5 | | | |
| Hydroxypropylcellulose | | | | 1.5 | 3.5 | 6 |
| Coating amount | 3 mg | 5 mg | 7 mg | 3 mg | 5 mg | 7 mg |

Production Examples 13 to 18

Orally disintegrating tablets containing the components in the amounts (mg) thereof per tablet shown in Table 7 can be conventionally produced.

Granules are produced through a wet granulation method using components between pemafibrate and aminoalkyl methacrylate copolymer K shown in Table 7. The obtained granules, and titanium oxide and the following components shown in Table 7 are mixed together, and the mixture is pelletized, whereby orally disintegrating tablets can be produced.

TABLE 7

| | Production Example 13 | Production Example 14 | Production Example 15 | Production Example 16 | Production Example 17 | Production Example 18 |
|---|---|---|---|---|---|---|
| Pemafibrate | 0.1 | 0.1 | 0.1 | 0.2 | 0.2 | 0.2 |
| D-mannitol | 16.6 | | 14.6 | | 14.6 | |
| Corn starch | | 14.6 | | 14.6 | | 14.6 |
| Crospovidone | 5.6 | | | | | |
| Crystalline cellulose | | 5.6 | | | | |
| Croscarmellose sodium | | | 5.6 | | | |
| Carmellose calcium | | | | 5.6 | | |
| Carmellose sodium | | | | | 5.6 | |
| Carmellose | | | | | | 5.6 |
| Hypromellose | 4.4 | 4.4 | 4.4 | 4.4 | 4.4 | 4.4 |
| Sucrose | 2.0 | 2.0 | 1.0 | 2.0 | 2.0 | 2.0 |
| 1-menthol | 0.4 | 0.4 | | 0.4 | 0.4 | 0.4 |
| Yellow ferric oxide | | | 0.05 | | | 0.1 |
| Aminoalkyl methacrylate copolymer E | | | | 3.0 | 3.0 | |
| Components above from the granule | | | | | | |
| Titanium oxide | 2.0 | | | 1.0 | | |
| Yellow ferric oxide | | 0.1 | | | 0.2 | |
| Light anhydrous silicic acid | | | 1.0 | | | 1.0 |
| D-mannitol | 40.0 | 42.6 | 43.6 | 42.0 | 40.0 | 40.0 |
| Xylitol | 3.0 | 3.0 | 3.0 | 3.0 | 3.0 | 3.0 |
| Crospovidone | | | | 12.9 | | |
| Microcrystalline cellulose | 55.0 | 55.0 | 50.0 | | | |
| Croscarmellose sodium | 12.9 | | | | 12.9 | |
| Carmellose calcium | | 12.9 | | | | 12.9 |
| Carmellose sodium | | | 12.9 | | | |
| Carmellose | | | | 55.0 | 55.0 | 55.0 |

TABLE 7-continued

| | Production Example 13 | Production Example 14 | Production Example 15 | Production Example 16 | Production Example 17 | Production Example 18 |
|---|---|---|---|---|---|---|
| Anhydrous dibasic calcium phosphate | 2.5 | 2.5 | 2.5 | 2.5 | 2.5 | 2.5 |
| Aminoalkyl methacrylate copolymer E | 3.0 | 3.0 | 2.0 | | | 3.0 |
| Yogurt Micron | 0.2 | | | 0.2 | | |
| Orange Micron | | 0.2 | 0.2 | | 0.2 | 0.2 |
| Calcium stearate | 0.8 | | 0.8 | 0.8 | 0.8 | |
| Magnesium stearate | | 0.8 | | | | 0.8 |

INDUSTRIAL APPLICABILITY

The present invention enables provision of a pharmaceutical composition having excellent storage stability and containing pemafibrate which exhibits plasma triglyceride concentration reducing action. HDL cholesterol increasing action, etc. The pharmaceutical composition can be used in, for example, pharmaceutical preparation industries.

The invention claimed is:

1. A solid pharmaceutical composition, comprising:

an active component comprising pemafibrate, a salt thereof or a solvate thereof; and at least one ester species selected from the group consisting of acetyltriethyl citrate, acetyltributyl citrate, triethyl citrate, tributyl citrate and triacetin, wherein the active component and the at least one ester species are formulated substantially in non-contact with each other such that the pemafibrate is substantially in non-contact with the at least one ester species, and wherein a total content of the at least one ester species with respect to 1 part by mass of a free form of pemafibrate is from 1 to 10 parts by mass.

2. The pharmaceutical composition according to claim 1, wherein the pharmaceutical composition has a dosage form that is a tablet, a capsule, a granule, a powder or a pill.

3. The pharmaceutical composition according to claim 1, wherein the at least one ester species is at least one selected from the group consisting of triethyl citrate and triacetin.

4. The pharmaceutical composition according to claim 1, further comprising:

at least one component incorporated such that the active component and the at least one ester species are formulated substantially in non-contact with each other by the at least one component and the pemafibrate is substantially in non-contact with the at least one ester species.

5. The pharmaceutical composition according to claim 4, wherein the at least one component comprises an additive component.

6. The pharmaceutical composition according to claim 1, further comprising:

a plurality of components incorporated such that the active component and the at least one ester species are formulated substantially in non-contact with each other by the components and the pemafibrate is substantially in non-contact with the at least one ester species.

7. The pharmaceutical composition according to claim 6, wherein the plurality of components comprises an additive component.

8. A pharmaceutical composition, comprising:

a film-coated tablet comprising a core tablet and a film coating layer, wherein the core tablet comprising an active component comprising pemafibrate, a salt thereof or a solvate thereof, and the film coating layer comprising at least one ester species selected from the group consisting of acetyltriethyl citrate, acetyltributyl citrate, triethyl citrate, tributyl citrate and triacetin are formulated such that the pemafibrate in the core tablet is substantially in non-contact with the at least one ester species, and wherein a total content of the at least one ester species with respect to 1 part by mass of a free form of pemafibrate is from 1 to 10 parts by mass.

9. The pharmaceutical composition of claim 8, wherein the core table comprises the active component and at least one binder selected from the group consisting of methylcellulose, hydroxypropyl cellulose, hypromellose, carmellose sodium, a starch selected from the group consisting of wheat starch, rice starch, corn starch, and partially pregelatinized starch dextrin, pullulan, acacia, agar, gelatin, tragacanth, sodium alginate, povidone and polyvinyl alcohol.

10. The pharmaceutical composition according to claim 8, wherein the core tablet comprises at least one component such that the active component in the core tablet and the at least one ester species in the film coating layer are formulated substantially in non-contact with each other by the at least one component and the pemafibrate is substantially in non-contact with the at least one ester species.

11. The pharmaceutical composition according to claim 10, wherein the at least one component comprises an additive component.

12. The pharmaceutical composition according to claim 8, wherein the core tablet comprises a plurality of components such that the active component in the core tablet and the at least one ester species in the film coating layer are formulated substantially in non-contact with each other by the components and the pemafibrate is substantially in non-contact with the at least one ester species.

13. The pharmaceutical composition according to claim 12, wherein the plurality of components comprises an additive component.

14. A pharmaceutical composition, comprising:

a film-coated tablet comprising a core tablet and a film coating layer, wherein the core tablet comprising an active component comprising pemafibrate, a salt thereof or a solvate thereof, and the film coating layer comprising at least one of a metal oxide, a dihydric alcohol and a silicic acid compound, and at least one ester species selected from the group consisting of acetyltriethyl citrate, acetyltributyl citrate, triethyl citrate, tributyl citrate and triacetin are formulated such that the pemafibrate is not in contact with the at least one of the metal oxide, the dihydric alcohol and the silicic acid compound, and the at least one ester species, and wherein a total content of the at least one ester species with respect to 1 part by mass of a free form of pemafibrate is from 1 to 10 parts by mass.

15. The pharmaceutical composition according to claim 14, wherein the core tablet comprises at least one component such that the active component in the core tablet and the at least one ester species and the at least one of the metal oxide, the dihydric alcohol, the silicic acid compound in the film coating layer are formulated substantially in non-contact with each other by the at least one component and the pemafibrate is substantially in non-contact with the at least one ester species.

16. The pharmaceutical composition according to claim 15, wherein the at least one component comprises an additive component.

17. The pharmaceutical composition according to claim 14, wherein the core tablet comprises a plurality of components such that the active component in the core tablet and the at least one ester species and the at least one of the metal oxide, the dihydric alcohol and the silicic acid compound in the film coating layer are formulated substantially in non-contact with each other by the components and the pemafibrate is substantially in non-contact with the at least one ester species.

18. The pharmaceutical composition according to claim 17, wherein the plurality of components comprises an additive component.

19. A method for stabilizing pemafibrate, a salt thereof or a solvate thereof in a pharmaceutical composition, comprising:

incorporating an active component comprising pemafibrate, a salt thereof or a solvate thereof, and at least one ester species selected from the group consisting of acetyltriethyl citrate, acetyltributyl citrate, triethyl citrate, tributyl citrate and triacetin such that the active component and the at least one ester species are formulated substantially in non-contact with each other such that the pemafibrate is substantially in non-contact with the at least one ester species, and wherein a total content of the at least one ester species with respect to 1 part by mass of a free form of pemafibrate is from 1 to 10 parts by mass.

20. The pharmaceutical composition according to claim 19, wherein the at least one ester species is at least one selected from the group consisting of triethyl citrate and triacetin.

* * * * *